United States Patent [19]

Schmidt et al.

[11] Patent Number: 5,473,058

[45] Date of Patent: Dec. 5, 1995

[54] PROCESS AND REAGENT FOR THE SPECIFIC DETERMINATION OF PANCREATIC α-AMYLASE

[75] Inventors: Axel Schmidt; Elli Rauscher, both of Munich; Herbert von der Eltz, Woilheim, all of Germany

[73] Assignee: Boehringer Mannheim GmbH, Mannheim-Waldhof, Germany

[21] Appl. No.: 109,678

[22] Filed: Aug. 20, 1993

Related U.S. Application Data

[62] Division of Ser. No. 577,480, Sep. 4, 1990, Pat. No. 5,264,345.

[30] Foreign Application Priority Data

Sep. 4, 1989 [DE] Germany ............... 39 29 355.6

[51] Int. Cl.[6] .................................. C07H 15/00
[52] U.S. Cl. ................. 536/17.9; 536/4.1; 536/17.2; 536/17.4; 536/18.4; 514/25
[58] Field of Search ................... 536/4.1, 17.2, 536/17.4, 18.7, 17.9, 18.4; 514/25

[56] References Cited

U.S. PATENT DOCUMENTS

| | | | |
|---|---|---|---|
| 4,316,983 | 2/1982 | Bollag et al. ............... | 536/17.2 |
| 4,454,315 | 6/1984 | Sasaki et al. ............... | 536/18.2 |
| 4,612,304 | 9/1986 | Fukushi ....................... | 514/53 |
| 4,963,479 | 10/1990 | Chavez et al. ............... | 435/22 |

FOREIGN PATENT DOCUMENTS 0298516  1/1989  European Pat. Off. .

*Primary Examiner*—Douglas W. Robinson
*Assistant Examiner*—Kathleen Kahler Fonda
*Attorney, Agent, or Firm*—Felfe & Lynch

[57] ABSTRACT

The present invention provides a process for the specific determination of pancreatic α-amylase in the presence of salivary α-amylase in body fluids by reaction with a system for the detection of α-amylase with the use of an inhibitor for salivary α-amylase, wherein, as substrate, there is used a compound of the general formula:—

(I)

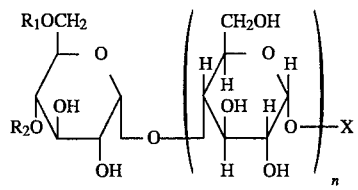

in which $R_1$ is a straight-chained or branched alkyl or alkoyl radical containing up to 6 carbon atoms, a cycloalkyl or cycloalkoxyl radical containing 3 to 6 carbon atoms or a benzoyl, benzyl or phenyl radical which is optionally hydrophilically substituted, $R_2$ is a hydrogen atom or in which $R_1$ and $R_2$ together form a methylene bridge, the hydrogen atoms of which, independently of one another, can each be substituted by an alkyl radical containing up to 5 carbon atoms or a phenyl radical, n is 1, 2 or 3 and X is an optically determinable residue. The present invention also provides a reagent for the specific determination of pancreatic α-amylase, as well as new compounds for use in the above process and reagent.

8 Claims, No Drawings

PROCESS AND REAGENT FOR THE SPECIFIC DETERMINATION OF PANCREATIC α-AMYLASE

This is a Divisional Application of application Ser. No. 07/577,480, filed Sep. 4, 1990, now U.S. Pat. No. 5,264,345.

The present invention is concerned with a process for the specific determination of pancreatic α-amylase in the presence of salivary α-amylase in body fluids by reaction with a system for the detection of α-amylase with the use of an inhibitor for salivary α-amylase, as well as a reagent suitable therefor.

α-Amylase (E.C. 3.2.1.1) preponderantly breaks down 1,4-α-glucosidically linked oligo- and polysaccharides by the random hydrolysis of the 1,4-α-glucosidic bonds to give maltose and maltooligosaccharides. Besides the industrial fermentation technology, the enzyme has considerable importance in the scope of clinical analysis and diagnosis.

α-Amylase essentially occurs in the body in two forms, namely, as pancreatic enzyme and as salivary enzyme. In the case of numerous diseases, the pancreatic α-amylase content in body fluids, such as serum, urine and duodenal secretion, changes considerably. Therefore, the problem exists of specifically determining pancreatic α-amylase without including salivary α-amylase also present in the fluid. The difficulty is that the two multiple forms have a similar construction and immunologically are very similar (see K. Lorenz, Laboratoriumsblätter, 32, 118/1982). For the elimination of the activity of the salivary enzyme, it has now been suggested (see Clin. Chem., 28/7, 1525–1527/1982) to inhibit the salivary enzyme by means of an inhibitor obtained from wheat germ. However, the selectivity is thereby unsatisfactory since, even in the case of optimum inhibitor concentration, about 13% of the activity of the salivary α-amylase is retained, whereas the activity of the pancreatic α-amylase is reduced to about 81%.

In published European Patent Specification No. A-0,191,284, it has now been suggested, for the specific determination of pancreatic α-amylase in the presence of salivary α-amylase, to use for the inhibition of the salivary α-amylase a monoclonal antibody which specifically inhibits the salivary enzyme but does not inhibit the pancreatic enzyme by more than 50%.

Furthermore, in published European Patent Specification No. A-0,150,309, it has already been suggested to determine pancreatic α-amylase in the presence of salivary α-amylase by working in the presence of a monoclonal antibody which reacts with salivary α-amylase and thereby shows a cross-reactivity of 5% or less with regard to pancreatic α-amylase. With this antibody, in the case of the addition of a precipitating agent, it is also possible to form an insoluble complex with the salivary α-amylase which can be separated from the solution so that only the pancreatic enzyme remains behind in the solution and can there be determined. Alternatively, it is possible to use the monoclonal antibody in immobilised form and, in this way, to separate off the salivary amylase. However, in both cases, it is necessary to form an insoluble phase and to separate it from the soluble phase.

A further improvement is provided by published European Patent Specification No. A-0,209,154 in which a combination of two antibodies is used, the first specifically inhibits the salivary enzyme to less than 97% and the second inhibits the enzyme to less than 10%. Pancreatic α-amylase can be determined very specifically with this process.

In the case of all of these known processes, detection systems must be used for the α-amylase which, besides a substrate, which is usually an oligomaltoside or modified starch, contain α-glucosidase as auxiliary enzyme. The use of an auxiliary enzyme is disadvantageous, on the one hand, for economic reasons and, on the other hand, because further sources of error are thereby introduced into the test.

It is an object of the present invention to provide a process for the specific determination of pancreatic α-amylase which, without the use of auxiliary enzymes, provides precise results more quickly and more simply.

Thus, according to the present invention, there is provided a process for the specific determination of pancreatic α-amylase in the presence of salivary α-amylase in body fluids by reaction with a system for the detection of α-amylase with the use of an inhibitor for salivary α-amylase, wherein, as substrate, there is used a compound of the general formula:—

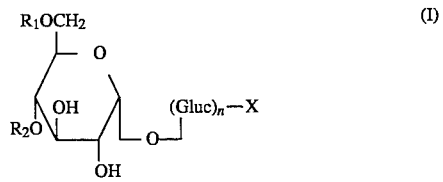

in which $R_1$ is a straight-chained or branched alkyl or alkoyl radical containing up to 6 carbon atoms, a cycloalkyl or cycloalkoxyl radical containing 3 to 6 carbon atoms or a benzoyl, benzyl or phenyl radical which is optionally hydrophilically substituted, $R_2$ is a hydrogen atom or in which $R_1$ and $R_2$ together form a methylene bridge, the hydrogen atoms of which, independently of one another, can each be substituted by an alkyl radical containing up to 5 carbon atoms or a phenyl radical, Gluc is a glucose molecule, n is 1, 2 or 3, and X is an optically determinable residue.

Surprisingly, the substrates used according to the present invention show a differentiation between the two isoenzymes. The substrates used according to the present invention have a higher activity for pancreatic α-amylase and make possible, in the case of combination with known inhibitors for salivary α-amylase, a very specific determination. By means of the use of this substrate, the amount of monoclonal antibody used as inhibitor can be considerably reduced.

The determination of pancreatic α-amylase takes place in known manner by reacting the body fluid with a substrate which, by reaction with α-amylase, forms an optically-active molecule, and an inhibitor for salivary α-amylase and then determining in known manner the colour formation, for example spectrophotometrically. The colour change is then a measure for the content of pancreatic α-amylase. The determination is carried out in body fluids, for example serum, urine or duodenal secretion. The sample solution is reacted with a substrate according to general formula I.

The substrates used according to the present invention are maltose, maltotriose or maltotetraose derivatives which are substituted on the reducing end with an optically-determinable residue and in which at least the hydroxyl group on the $C_6$-atom of the non-reducing end is derivatised. For this purpose, on the non-reducing end, the hydrogen atom of the hydroxyl group is substituted by the radical $R_1$. $R_1$ can be an alkyl radical containing up to 6 carbon atoms, appropriate examples of which include methyl, ethyl, propyl, isopropyl, butyl, isobutyl, tert.-butyl and n-pentyl radicals and the isomers thereof, as well as the n-hexyl radical and the isomers thereof. As substituents, there can also be used the alkoyl radicals corresponding to the mentioned alkyl radicals. In addition, there can be used cycloalkyl and cycloalkoyl radicals containing 3 to 6 carbon atoms and especially the cyclopropanoyl and cyclopropyl radicals. These radicals can possibly be hydrophilically substituted in order to increase the water-solubility of the substrate. As $R_1$, there can also be used an optionally hydrophilically substituted benzoyl, benzyl or phenyl radical. Appropriate hydrophilic substituents include, in particular, carboxyl, hydroxyl, sulphonic acid, dimethylamino, phosphate, halogen and/or nitro groups, for example the dimethylsuccinate radical. When $R_1$ signifies one of the above-mentioned radicals, then the hydroxyl group in the 4-position of the terminal glycoside residue remains unsubstituted.

In a further embodiment of the present invention, the oxygen atoms in the 4- and 6-positions of the terminal glycosyl residue are bridged by a methylene bridge, the hydrogen atoms of which, possibly independently of one another, can be substituted by an alkyl radical or a phenyl radical. Substrates are preferably used in which $R_1$ is an acetyl or isobutyryl radical or in which $R_1$ and $R_2$ together form an ethylidene or benzylidene radical.

The substrates used according to the present invention can contain 2 to 4 glucose units which are linked together 1,4-glucosidically. Substrates are preferred with 2 or 3 glucose units, maltotriose derivatives being especially preferred.

On the reducing end, the substrates according to the present invention carry an optically-determinable radical X, the radical X being attached α-glycosidically to the terminal oxygen atom. The radical is thereby one which is coloured in the visible or ultra-violet range or is a radical which becomes optically determinable by reaction with a further compound, for example by conversion into a coloured material or by coupling to a coloured material. Such optically-determinable radicals are well known. Preferred are resorufin, chlorophenol red, azo dyestuffs, azamethine and styryl dyestuffs and nitrophenols mono- or disubstituted in the ortho-position, as well as umbelliferones. As optically-determinable residues, there is especially preferred resorufin and nitrophenols mono- or disubstituted in the ortho-position, especially nitrophenols substituted with ester groups or (pseudo) halogen atoms. The preparation of the oligomaltoside derivatives used as substrates according to the present invention takes place according to known methods. Starting from oligoglucosides with 2 to 4 glucose units, the preparation can take place by reacting these under etherification conditions with a dialkoxy compound, preferably with a dialkoxyethane or a corresponding benzyl derivative, with the formation of a compound of general formula (I) in which $R_1$ and $R_2$ together form an optionally substituted methylene radical.

Into the unprotected substrate, there can also be introduced the desired activation group via activated carboxylic acid groups, for example via the corresponding ortho esters, acid chlorides, anhydrides, from activated esters enzymatically (see J.A.C.S., 110, 584–589/1988), from acetals or directly from the carboxylic acids via water-removing agents, for example by the Mitsunobu reaction (see Tetrahedron Letters, 30, 325–326/1989). Especially preferred is the enzymatic preparation via the corresponding ortho esters as intermediates or the preparation via the Mitsunobu reaction. The ortho esters are preferably prepared from the corresponding nitriles (cf., for example, Houben-Weyl, Vol. VI/3, 300–313/1965). The purification of the protected substrates can take place, for example, chromatographically via ion exchangers or MPLC.

The determination of pancreatic α-amylase takes place in the presence of an inhibitor for salivary α-amylase, antibodies preferably being used for the inhibition of salivary α-amylase. For example, there can be used monoclonal antibodies which specifically inhibit the salivary enzyme but which inhibit the pancreatic enzyme by not more than 50%. Such antibodies are described in published European Patent Specification No. A-0,191,284. In a further embodiment, as inhibitor there is used a monoclonal antibody which reacts with salivary α-amylase and thereby shows a cross-reactivity of 5% or less with regard to pancreatic α-amylase. Such antibodies are described in published European Patent Specification No. 0,150,309. As inhibitor for salivary α-amylase, there is especially preferably used a combination, described in published European Patent Specification No. 0,209,154, of a first monoclonal antibody, which specifically inhibits the salivary enzyme by less than 97%, and a second monoclonal antibody which inhibits this enzyme by less than 10%. The first antibodies are produced, for example, from the cell lines NCACC 84122003 and 84122004 and the latter by the cell lines 84111301 and 84111302.

Due to the combination according to the present invention of the substrate and of the inhibitor, the determination of pancreatic α-amylase takes place very selectively and very precisely.

The process according to the present invention can also take place with the addition of an-activator. Activators which influence the activity of α-amylase are known. Azides are known for this purpose and they can also be used in the present case. However, as activators, there are especially preferably used thiocyanate-containing compounds. We have found that these compounds bring about a further improvement in favour of the pancreatic α-amylase. The activator can be used in an amount of from 50 to 700 mmole/liter and preferably of from 200 to 500 mmole/liter.

The present invention also provides a reagent for the specific determination of pancreatic α-amylase in the presence of salivary α-amylase, wherein, as substrate, it contains a compound of the general formula:—

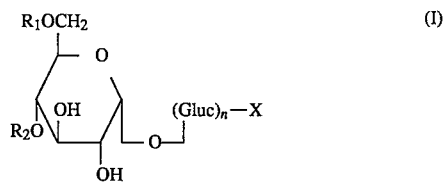

(I)

in which $R_1$ is a straight-chained or branched alkyl or alkoyl radical containing up to 6 carbon atoms, a cycloalkyl or cycloalkoyl radical containing 3 to 6 carbon atoms or a benzoyl, benzyl or phenyl, in each case optionally substituted hydrophilically, $R_2$ is a hydrogen atom or $R_1$ and $R_2$ together form a methylene bridge, the hydrogen atoms of which, independently of one another, can each be substituted by an alkyl radical containing up to 5 carbon atoms or a phenyl radical, Gluc is a glucose molecule, n is 1, 2 or 3 and X is an optically-determinable residue.

Furthermore, the present invention provides compounds which can be used for the process according to the present invention and which have the general formula:—

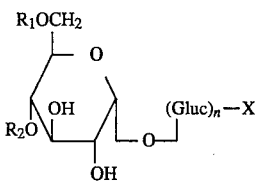

wherein Gluc is a glucose molecule, X is an optically-determinable residue and, when n is 1, $R_1$ is a straight-chained or branched alkyl or alkoyl radical containing up to 6 carbon atoms or an optionally hydrophilically-substituted cycloalkyl or cycloalkoyl radical containing 3 to 6 carbon atoms or a benzoyl, benzyl or phenyl radical, $R_2$ is a hydrogen atom or $R_1$ and $R_2$ together form a methylene bridge, the hydrogen atoms of which, independently of one another, can each be substituted by an alkyl radical containing up to 5 carbon atoms or a phenyl radical or wherein n is 2 or 3 and $R_1$ is a straight-chained or branched alkyl radical containing up to 6 carbon atoms or an optionally hydrophilically-substituted cycloalkyl radical containing 3 to 6 carbon atoms, a phenyl radical or a benzyl radical and $R_2$ is a hydrogen atom.

According to the present invention, there is provided a process and a reagent, as well as an appropriate substrate, with which pancreatic α-amylase can be determined very specifically in the presence of salivary α-amylase. By combination of the substrate used with inhibitors, the specificity can be further improved in the case of a simultaneously very high sensitivity of the process.

The following Examples are given for the purpose of illustrating the present invention:

Example 1.

Synthesis of α-D-maltotrioside dye stuff substrates.

10 mmole of peracetylated maltotriose, 15 mmole of an appropriate phenolic dye and 11 mmole of boron trifluoride etherate ($BF_3 \cdot OEt_2$) are stirred in a mixture of 25 ml. anhydrous toluene and 5 ml. anhydrous dichloroethane for 32 hours at 45° C. with the exclusion of moisture, whereby, after 8 hours, a further 11 mmole of boron trifluoride etherate are added thereto.

The reaction mixture is subsequently carefully mixed with 100 ml. of a saturated aqueous solution of sodium carbonate, 60 ml. dichloromethane are added thereto and, after vigorous stirring, the organic phase is separated off. After washing twice with, in each case, 100 ml. of water and drying over anhydrous magnesium sulphate, the organic phase is removed by evaporation under reduced pressure. The residue is dissolved in a mixture of 130 ml. methanol, 50 ml. chloroform and 13 ml. concentrated hydrochloric acid and stirred for 48 hours at ambient temperature. Subsequently, the solution is mixed with 100 ml. of water and 20 ml. dichloromethane and the aqueous phase is separated off. After adjustment to pH 6.5 with a 4N aqueous solution of sodium hydroxide, the water is removed under reduced pressure and the residue is applied to a Diaion column (polystyrene). The column is washed with 800 ml. of water and the product is eluted with a 30% isopropanol solution. The eluate is evaporated and the residue is fracionally chromatographed over an MPLC column (RP-18) with 13% isopropanol. The fractions which contain the product are pooled concentrated in vacuo and fractionally chromatographed over Sephadex LH-20 with water The fractions which contain the product are combined, concentrated in vacuo and subsequently lyophilised.

Example 2.

Synthesis of 2-chloro -4-nitrophenyl-α-D-maltotrioside, derivatised at the terminal (nonreducing) D-glucosyl group 0.45 mmole of 2-chloro-4-nitrophenyl-maltotrioside, 0.55 mmole of an appropriate ortho ester and 0.51 mmole of anhydrous p-toluenesulphonic acid are stirred for 2 hours in 3 ml. of anhydrous dimethylformamide with the exclusion of moisture. The reaction mixture is mixed with 15 ml. of a 20% isopropanol solution, adjusted with 6N hydrochloric acid to pH 3.0 and stirred for 30 minutes at ambient temperature. After filtration over a Seitz filter, and washing of the filter with 20% isopropanol and the filtrate is evaporated in vacuo and the residue is fractionally chromatographed over an MPLC column (RP-18) with an isopropanol solution (see the following Table 2). The fractions which contain the product are combined, evaporated in vacuo and lyophilised.

TABLE 1

| activation group | % isopropanol for MPLC (RP-18) | yield | HPLC (1 ml./min.) (RP-18, 280 nm) RT/% isopropanol |
|---|---|---|---|
| acetate | 13% | 32% | 6.76/17% |
| isobutyrate | 17% | 30% | 6.95/25% |
| cyclopropyl-carboxylate | 15% | 10% | 6.90/25% |
| dimethyl-succinate | 10% | 21% | 8.49/10% |

The maltotriosides described in the following Table 2 and derivatised with other dye stuff are also prepared by the above-described process:

TABLE 2

| coloured material | HPLC (amino) 1 ml./min./$R_1$ 280 nm RT/acetonitrile |
|---|---|
| 2-cyano-4-nitrophenol | 5.80/75% |
| 2-chloro-4-nitrophenol | 5.89/75% |
| 2-flouro-4-nitrophenol | 6.23/75% |
| 2-bromo-4-nitrophenol | 5.33/75% |
| 2-triflouromethyl-4-nitrophenol | 7.16/17% (RP-18 column) |

Example 3.

The amylase activity of human pancreatic α-amylase (HPA) and of human salivary α-amylase (HSA) is investigated with various substrates shown in Table 3. The following reagents were used:

| Reagent 1: | |
|---|---|
| 4-morpholine ethanesulphonate (= MES) buffer | 61.6 mmole/liter |
| containing sodium chloride | 57.1 mmole/liter |

-continued

| Reagent 1: | |
|---|---|
| calcium acetate | 5.6 mmole/liter |

Reagent 1 optionally also contains activator, as given in Table 3, as well as possibly antibodies produced by the cell lines NCACC 84122003 (MAB I) and NCACC 84111301 (MAB II). For carrying out the determination, 1.00 ml. of Reagent 1 is mixed with 0.02 ml. of sample and warmed to 37° C. Subsequently, 0.10 ml. of Reagent 2 is added thereto, mixed and, after 1, 2 and 3 minutes, the extinction is read off at 405 nm. There is obtained the average value of the absorbance change/minute ($\Delta A$/min.)

Calculation:

$$U/L \text{ sample} = \frac{\Delta A/\text{min} \times 1.12 \times 1000}{\epsilon \times 0.02}$$

The final concentrations in the test batch amount to:

| | |
|---|---|
| MES buffer | 55 mmole/liter |
| sodium chloride | 51 mmole/liter |
| calcium acetate | 5 mmole/liter |
| substrate | 4.44 mmole/liter |
| optionally activator sodium azide | 152 mmole/liter |
| or potassium thiocyanate | 400 mmole/liter |
| MAB I | about 5 to 8 mg./liter |
| MAB II | about 2 to 3 mg./liter |

The results obtained are given in the following Table 3:

TABLE 3

Direct amylase substrates
Determination of the amylase activity in human pancreatic amylase (HPA)
and human salivary amylase (HSA)
Test conditions as described in published European Patent Specification No. A-0,263,435:
MES-buffer 55 mmol/l. (pH 6.0)/NaCl 51 mmol/l., calcium acetate 5 mmol/l.,
substrate 4.44 mmol/l. (final concentration in the assay)
Sample dilution 1:56
Measurement at 37° C. at 405 nm
Evaluation via the absorbance coefficients of the chromophore

| substrate | without addition | | 152 mmol/l. NaN$_3$ | | 400 mmol/l. KSCN | |
|---|---|---|---|---|---|---|
| | HPA | HSA | HPA | HSA | HPA | HSA |
| | U/l | U/l | U/l | U/l | U/l | U/l |
| 2-chloro-4-nitrophenylmaltoside | 13 | 7 | 68 | 50 | 50 | 40 |
| 2-chloro-4-nitrophenylmaltotrioside | 123 | 52 | 375 | 371 | 384 | 405 |
| 2-fluoro-4-nitrophenylmaltotrioside | 46 | 32 | 196 | 205 | 133 | 140 |
| 2-bromo-4-nitrophenylmaltotrioside | 132 | 105 | 336 | 362 | | |
| isobutyryl derivative of 2-chloro-4-nitrophenylmaltotrioside | 181 | 121 | 387 | 237 | 234 | 184 |
| acetyl derivative of 2-chloro-4-nitrophenylmaltotrioside | 224 | 98 | 566 | 308 | 579 | 418 |
| MAB I and MAB II | | | | | | |
| with 2-chloro-4-nitrophenylmaltotrioside | 186 | 11 | 372 | 10 | 336 | 6 |
| with the isobutyryl derivative | | | 399 | 4 | | |
| with the acetyl derivative | 206 | 13 | 510 | 6 | 559 | 13 |

The values obtained show that, in the case of the use of the process according to the present invention, the pancreatic enzyme is more strongly activated than the salivary enzyme. In combination with an inhibitor for salivary amylase, the specificity is very high. This effect is further increased by the addition of potassium thiocyanate.

Example 4.

Enzymatic synthesis of α-D-maltotrioside-resorufin.

a) Synthesis of resorufin-α-D-glucoside.

5 mmole of N,O-diacetylleukoresorufin and 5 mmole 1,2-anhydro-α-D-glucopyranose triacetate are heated under reflux in anhydrous toluene with the exclusion of moisture until the reaction is complete. In general, the reaction is completed after 8 to 12 hours. The toluene is distilled off in vacuo and the residue is taken up in 200 ml. ethyl acetate. After washing the ethyl acetate solution with a saturated aqueous solution of sodium bicarbonate (2×200ml) and 200ml. of water, the solution is dried over anhydrous magnesium sulphate and removed in vacuo. The residue thus obtained is hydrolysed for 16 hours at ambient temperature in a mixture of 13 ml. chloroform, 3.2 ml. concentrated hydrochloric acid and 32 ml. of methanol. The solution is subsequently concentrated in vacuo to about 10 ml., diluted with water to 40 ml., the pH is adjusted to 6.5 and applied to polystyrene (Diaion HP 20). The column is washed with 4 liters of water and the product is eluted with a 30% solution of isopropanol. The eluate is concentrated in vacuo to 20 ml. and fractionally chromatographed over an MPLC column (see below) with 13% isopropanol. The fractions which contain the product are combined, concentrated in a vacuum and lyophilised. Yield 300 mg. (15% of theory) of orange-coloured lyophilisate. Retention time: 5.46 (reverse phase column 40 μ, RP 18; HS-Sil®, Labomatic) 13% isopropanol/1 ml./min.

b) Enzymatic synthesis.

330 mg. Resorufin-α-D-glucoside and 4.96 g. cyclodextrin are dissolved in 16.5 ml. dimethylformamide, mixed with 165 ml. of buffer (0.05 mole/liter sodium citrate/0.005 mole/liter calcium chloride; pH 5.0) and 0.568 KU cyclodextrin glucanotransferase (E.C. 2.4.1.19) added thereto. The reaction mixture is stirred for 2 hours at ambient temperature and the enzyme activity then stopped, for example with Velcorin® (Bayer AG). By HPLC chromatography (13% isopropanol reverse phase column 5 μ, RP-18; Nucleosil®, Machery & Nagel) there is obtained the following distribution pattern:

| | |
|---|---|
| resorufin-α-D-glucoside | 26.9% |
| resorufin-α-D-maltoside | 16.0% |
| resorufin-α-D-maltotrioside | 25.3% |
| resorufin-α-D-maltotetraoside | 12.2% |
| resorufin-α-D-maltopentaoside | 15.2% |
| and higher | 4.3% |

The solution is dried over a special filter, concentrated in vacuo to 10 ml. and fractionally chromatographed over an MPLC column (conditions as in Example 4a)). The fractions which contain the desired product are combined, concentrated in vacuo and lyophilised to give an orange-coloured lyophilisate. Retention time: 4.26 (conditions as in Example 4a)).

We claim:

1. A compound of the general formula:

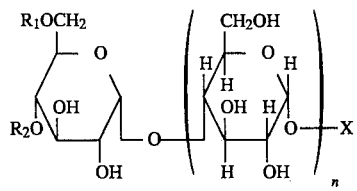

(I)

wherein

X is an optically determinable residue that is α-glycosidically bound to the terminal oxygen atom;

n is 1 or 2;

and when n is 1, $R_1$ is selected from the group consisting of
(a) a straight-chained or branched alkyl or alkoyl group containing up to 6 carbon atoms,
(b) a cycloalkyl or cycloalkoyl group containing 3 to 6 carbon atoms,
(c) a hydrophilically substituted cycloalkyl or cycloalkoyl group containing 3–6 carbon atoms, or
(d) a benzyl, benzoyl or phenyl group and $R_2$ is a hydrogen atom or $R_1$ and $R_2$ together form a methylene bridge, the hydrogen atoms of which, independently of one another, can each be replaced by an alkyl group containing up to 5 carbon atoms or a phenyl group and, when n is 2, $R_1$ is selected from the group consisting of
(a) a straight-chained or branched alkyl group containing up to 6 atoms,
(b) a cycloalkyl radical containing 3 to 6 carbon atoms,
(c) a hydrophilically substituted cycloalkyl group containing 3–6 carbon atoms, or
(d) a phenyl radical or a benzyl radical, and $R_2$ is a hydrogen atom.

2. A compound of the general formula:

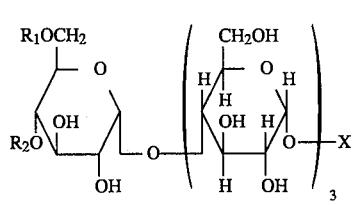

(I)

wherein

X is an optically-determinable residue that is α-glycosidically bound to the terminal oxygen atom and is selected from the group consisting of resorufin, chlorophenol red, an azo dye, an azamethine dye, a styryl dye, a nitrophenol mono- or di-substituted in the ortho position and an umbelliferone 1, $R_1$ is selected from the group consisting of
(a) a straight-chained or branched alkyl or alkoxy group containing up to 6 carbon atoms,
(b) a cycloalkyl or cycloalkoyl radical containing 3 to 6 carbon atoms, or
(c) a hydrophilically substituted benzoyl or phenyl radical, and $R_2$ is a hydrogen atom or $R_1$ and $R_2$ together form a methylene bridge, the hydrogen atoms of which, independently of one another, can each be replaced by an alkyl group containing up to 5 carbon atoms or a phenyl group.

3. A compound of claim 1, wherein X is 2-chloro-4-nitrophenyl.

4. A compound of claim 2, wherein X is 2-chloro-4-nitrophenyl.

5. A compound of claim 2, wherein X is 2-fluoro-4-nitrophenyl.

6. A compound of claim 2, wherein X is 2-bromo-4-nitrophenyl.

7. A compound of claim 4, wherein R1 is isobutyryl.

8. A compound of claim 4, wherein R1 is acetyl.

* * * * *